(12) United States Patent
Pasquet

(10) Patent No.: US 8,128,664 B2
(45) Date of Patent: Mar. 6, 2012

(54) INTERVERTEBRAL IMPLANT FOR LUMBOSACRAL JOINT

(75) Inventor: Denis Pasquet, Quinsac (FR)

(73) Assignee: Zimmer Spine, Bordeaux (FR)

( * ) Notice: Subject to any disclaimer, the term of this patent is extended or adjusted under 35 U.S.C. 154(b) by 710 days.

(21) Appl. No.: 11/910,691

(22) PCT Filed: Apr. 6, 2006

(86) PCT No.: PCT/FR2006/050304
§ 371 (c)(1),
(2), (4) Date: Jan. 27, 2009

(87) PCT Pub. No.: WO2006/106268
PCT Pub. Date: Oct. 12, 2006

(65) Prior Publication Data
US 2009/0216276 A1    Aug. 27, 2009

(30) Foreign Application Priority Data
Apr. 7, 2005   (FR) ...................................... 05 03462

(51) Int. Cl.
*A61B 17/70* (2006.01)
(52) U.S. Cl. ........................................ 606/249; 606/261
(58) Field of Classification Search .......... 606/246–265, 606/266–279; 623/17.11, 17.14–17.16
See application file for complete search history.

(56) References Cited

U.S. PATENT DOCUMENTS

| | | | |
|---|---|---|---|
| 5,306,275 A * | 4/1994 | Bryan ........................... | 606/914 |
| 6,749,613 B1 * | 6/2004 | Conchy et al. .................. | 606/57 |
| 6,786,907 B2 * | 9/2004 | Lange ........................... | 606/250 |
| 7,066,938 B2 * | 6/2006 | Slivka et al. .................. | 606/914 |
| 2003/0028250 A1 * | 2/2003 | Reiley et al. ................. | 623/17.11 |
| 2003/0114853 A1 * | 6/2003 | Burgess et al. ................. | 606/61 |
| 2004/0049188 A1 * | 3/2004 | Slivka et al. .................. | 606/61 |
| 2005/0033434 A1 * | 2/2005 | Berry ........................... | 623/17.14 |
| 2005/0080414 A1 * | 4/2005 | Keyer et al. .................... | 606/61 |
| 2005/0119657 A1 * | 6/2005 | Goldsmith ...................... | 606/61 |
| 2005/0191409 A1 * | 9/2005 | Murrell et al. .................. | 427/8 |
| 2006/0084976 A1 * | 4/2006 | Borgstrom et al. ............. | 606/54 |
| 2006/0149230 A1 * | 7/2006 | Kwak et al. .................... | 606/61 |

FOREIGN PATENT DOCUMENTS

| | | |
|---|---|---|
| EP | 1138268 A1 | 10/2001 |
| FR | 2714591 A1 | 7/1995 |
| FR | 2775183 A1 | 8/1999 |
| FR | 2799948 A1 | 4/2001 |
| WO | 2005020860 A2 | 3/2005 |
| WO | 2006110578 A2 | 10/2006 |

\* cited by examiner

*Primary Examiner* — Eduardo C Robert
*Assistant Examiner* — Atiya Mahmud
(74) *Attorney, Agent, or Firm* — Seager Tufte & Wickhem LLC

(57) ABSTRACT

The invention relates to an implant for placing between the sacrum of a patient and the fifth lumbar vertebra. It comprises a connection bar (22), fastener means (24, 26) for fastening each end of the connection bar to the sacrum, and a spacer (20) having a first end for co-operating with the spinous process of the fifth lumbar vertebra, and a second end for co-operating with said connection bar, the implant being characterized in that said connection bar (22) has two ends (38, 40) presenting a common first geometrical axis, and a middle portion (36) connected to said ends, said middle portion lying on a second geometrical axis parallel to the first geometrical axis but offset relative thereto, second end of the spacer co-operating with said middle portion.

8 Claims, 4 Drawing Sheets

INTERVERTEBRAL IMPLANT FOR LUMBOSACRAL JOINT

BACKGROUND OF THE INVENTION

The present invention relates to an intervertebral implant for the lumbo-sacral joint.

In the anatomy of the spine, the sacrum, which is situated below the lumbar vertebrae, is constituted by five vertebrae which, during human evolution, have become fused together. The top vertebra of the sacrum, written S1, is jointed to the fifth lumbar vertebra, written L5. This joint thus constitutes the lumbo-sacral joint, or L5-S1 joint, as shown in accompanying FIG. 1.

Each lumbar vertebra presents a middle, posterior projection: the "spinous process", referred to below as the process 10. The sacral vertebrae have lost their processes over evolution, and instead they retain only respective small residual bosses 12.

In man, certain back pains can be due to stresses associated with relative displacements between two vertebrae acting on the intervertebral disk that is situated between those two vertebrae.

DESCRIPTION OF THE PRIOR ART

Numerous intervertebral implants are already known that seek to limit the displacement between two vertebrae so as to relieve the intervertebral disk, and in particular the implant described in document FR 2 775 183. That implant is a spacer presenting in its top and bottom faces two longitudinal recesses both oriented in the same direction, that of the midplane of the spacer, and designed to receive the processes of the adjacent vertebrae, between which the spacer is to be implanted. The spacer is then held in position by straps surrounding said processes. By blocking a portion of the spine, the spacer transfers load above and below the vertebrae in question, thereby relieving the intervertebral disk situated between the vertebrae. However, because of the anatomy of the sacral region, and more particularly because of the lack of a process on the vertebra S1, it is not possible to put a spacer of that type into place over the L5-S1 joint.

Also known is a type of implant as described in document EP 1 138 268, that is specifically adapted to the anatomy of the lumbar-sacral region. That implant comprises an intervertebral spacer and a connection bar. The intervertebral spacer has two recesses that are substantially mutually orthogonal, and the connection bar is secured to the sacrum by means of two hooks fastened to the vertebra S1. More precisely, the hooks bear against the top portion of the vertebra S1, also known as the posterior arc, and they are fastened to the sacrum by respective fastener means such as staples that enable the hooks to be positioned and stabilized. Once the hooks are installed on the sacrum, the bar is fastened to the hooks and the intervertebral spacer is put into place. The top recess of the spacer is suitable for receiving the process of the vertebra L5, and its bottom recess is of a shape suitable for receiving the bar, so that the spacer rests on the bar.

Nevertheless, that type of implant presents certain drawbacks. Firstly, to enable the bottom notch of the spacer to be engaged on the connection bar, it is necessary for it to be far enough away from the sacrum. As a result, firstly the implant is relatively bulky, and secondly the connection between the bottom end of the spacer and the bar is uncertain. In addition, and above all, it is not easy for the surgeon to put the spacer into place between the connection bar and the spinous process of the fifth lumbar vertebra. In order to ensure that the ends of the spacer are held by the process and on the connection bar, it is necessary for the two notches disposed in the ends of the spacer to be sufficiently deep. It is therefore necessary to space the sacrum and the fifth lumbar vertebra apart by a relatively large amount.

SUMMARY OF THE INVENTION

To remedy those drawbacks, an object of the present invention is to provide an intervertebral implant for the lumbo-sacral joint that holds in place better and that makes it easier for a surgeon to put said implant into place.

According to the invention, to achieve this object, the implant for being placed between the sacrum of a patient and the fifth lumbar vertebra comprises a connection bar, means for fastening each end of the connection bar to the sacrum, and a spacer having a first end for co-operating with the spinous process of the fifth lumbar vertebra, and a second end for co-operating with said connection bar, the implant being characterized in that said connection bar has two ends lying on a common first geometrical axis and a middle portion connected to said ends, said middle portion lying on a second geometrical axis parallel to the first geometrical axis but offset relative therefrom, the second end of the spacer co-operating with said middle portion.

It will be understood that because of the special shape of the connection bar, which shape is somewhat like a crankshaft, it is possible, when putting the spacer into place, to give the middle portion of the connection bar a position that is suitable for making it easier to put the spacer into place.

In a preferred embodiment, the implant is characterized in that the ends of said connection bar are of circular right section and in that each fastener means for fastening the connection bar to the sacrum includes a head suitable for pivotally receiving one of the ends of said bar and a locking member suitable, in its active position, for preventing said end of the bar from pivoting.

It will be understood that because of the combination of characteristics specified above, it is possible to begin by giving the connection bar an angular orientation for its middle portion that is spaced apart from the sacrum so as to make it easier to put the bottom end of the spacer into place, and then to cause said middle portion to pivot about the main axis of the connection bar so as to bring it into the correct position.

Preferably, the implant is characterized in that said second end of the spacer includes a recess for receiving the middle portion of the bar, said recess allowing said spacer to pivot freely about the second geometrical axis of the middle portion of the bar.

It will also be understood that because of the combination of the above-specified characteristics, it is possible not only to cause the connection bar to pivot about its main axis as to bring its middle portion into an appropriate final position, but that it is also possible to cause the entire spacer to pivot about the middle portion of the connection bar so as to bring the top portion of the spacer into contact with the spinous process of the fifth lumbar vertebra.

Also preferably, the recess provided at the bottom end of the spacer includes means for snap-fastening the middle portion of the bar to the bottom end of the spacer, thereby further simplifying the actions of the surgeon.

BRIEF DESCRIPTION OF THE DRAWINGS

Other characteristics and advantages of the invention appear better on reading the following description of embodiments of the invention given as non-limiting examples. The description refers to the accompanying figures, in which.

DETAILED DESCRIPTION OF THE PREFERRED EMBODIMENTS

Figure 1:
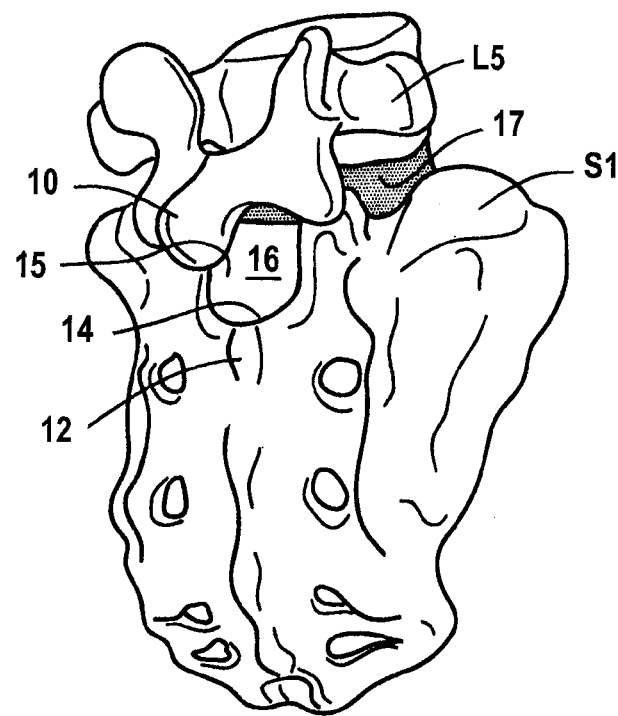
FIG. 1, described above, describes the lumbo-sacral joint.
Figure 2A:
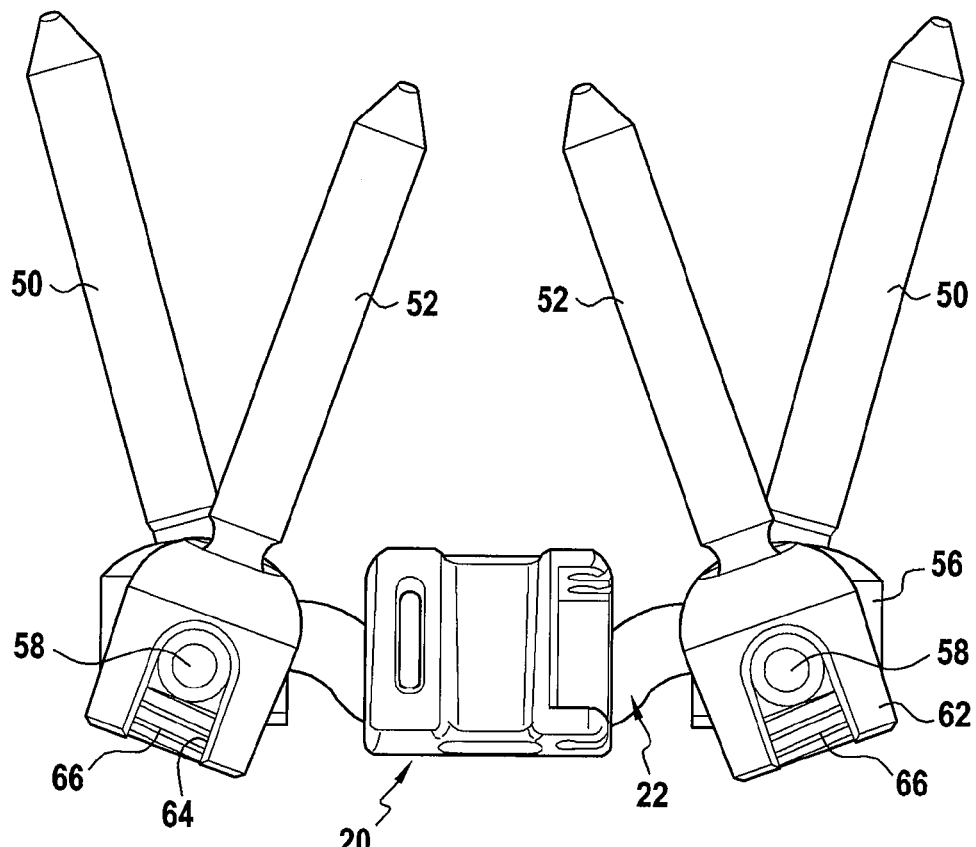
FIG. 2A is a plan view of the implant of the invention.
Figure 2B:
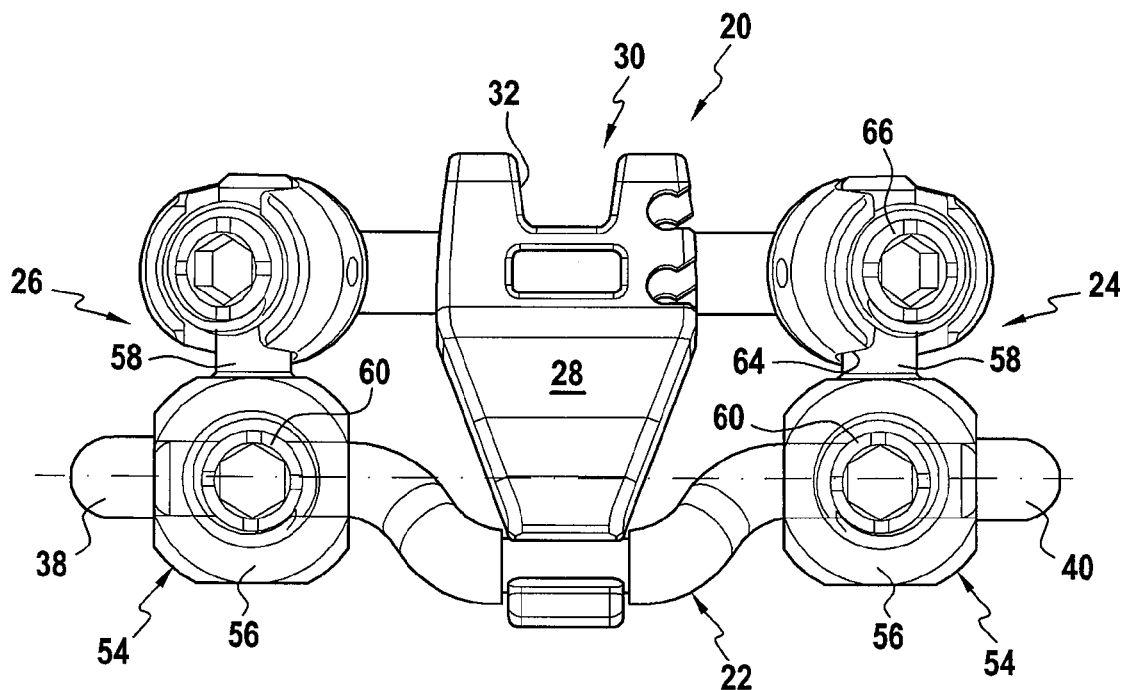
FIG. 2B is an elevation view of the implant.
Figure 2C:
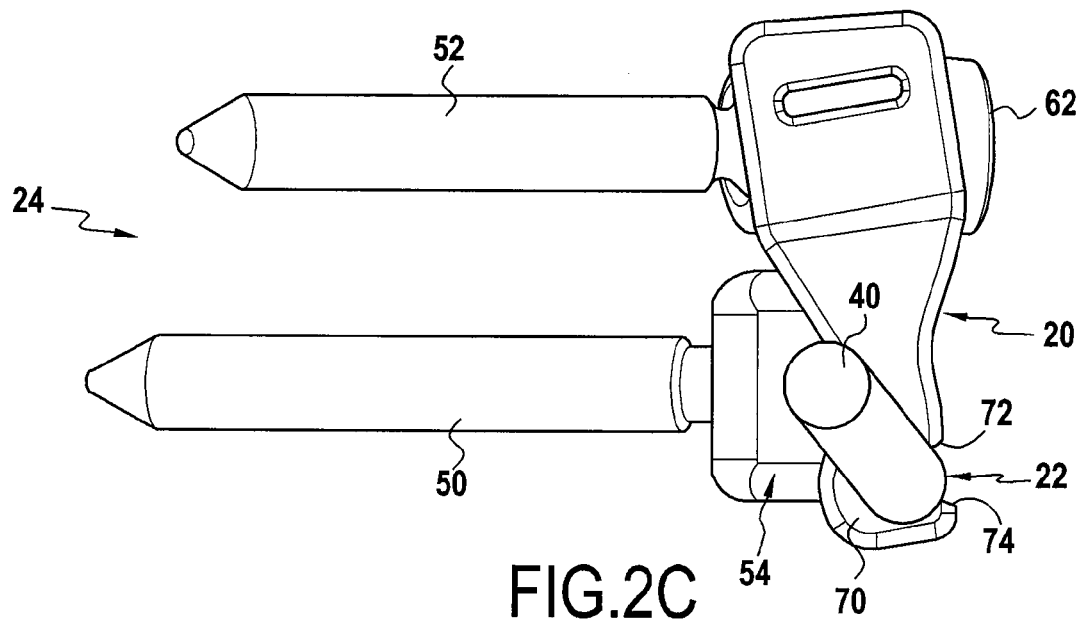
FIG. 2C is a side view of the implant.
Figure 3:
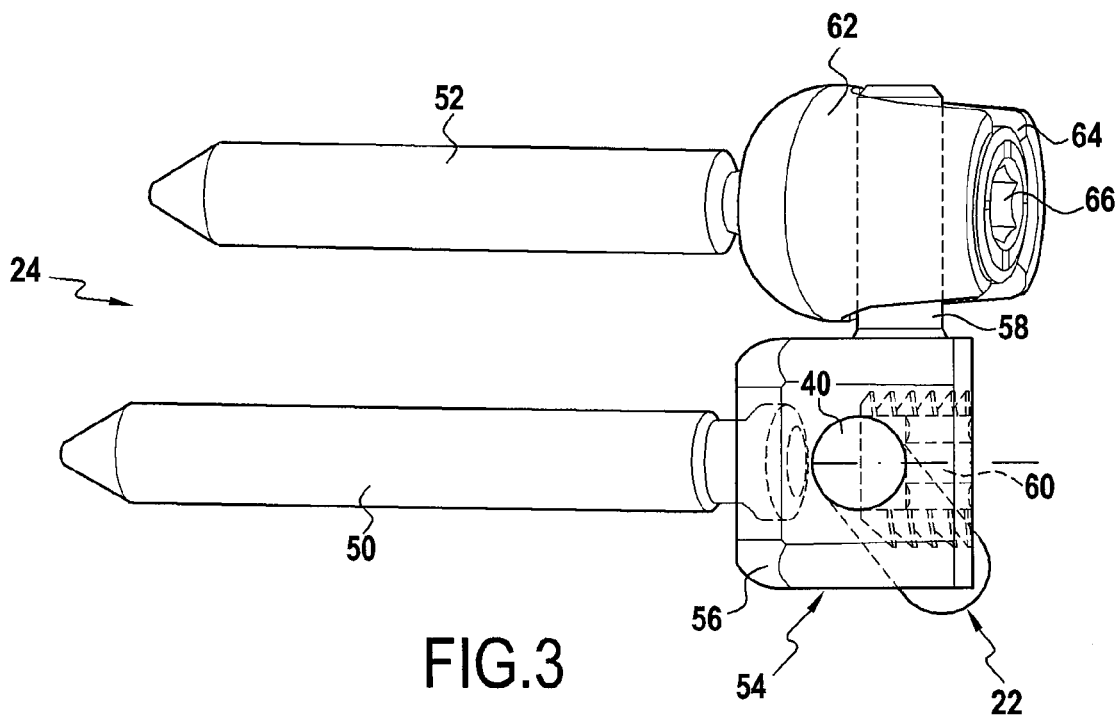
FIG. 3 is an elevation view of two types of screw used in the implant of the invention.

With reference initially to FIGS. 2A, 2B, and 2C, there follows a description of the component elements of the intervertebral implant for the lumbo-sacral joint.

The implant is constituted essentially by an intervertebral spacer 20, a connection bar 22, and two fastener systems 24 and 26 for fastening the connection bar 22 to the sacrum.

The spacer 20 comprises a body 28, a top end 30 of standard shape for an intervertebral spacer, i.e. provided with a recess 32 for receiving the spinous process 10 of the fifth lumbar vertebra, and a bottom end 34 for co-operating with the connection bar 22.

The connection bar 22 has a middle portion 36 that co-operates with the second end 34 of the intervertebral spacer 20, and two fastener ends 38 and 40 that co-operate with the respective fastener systems 24 and 26 in the sacrum.

Figure 5:
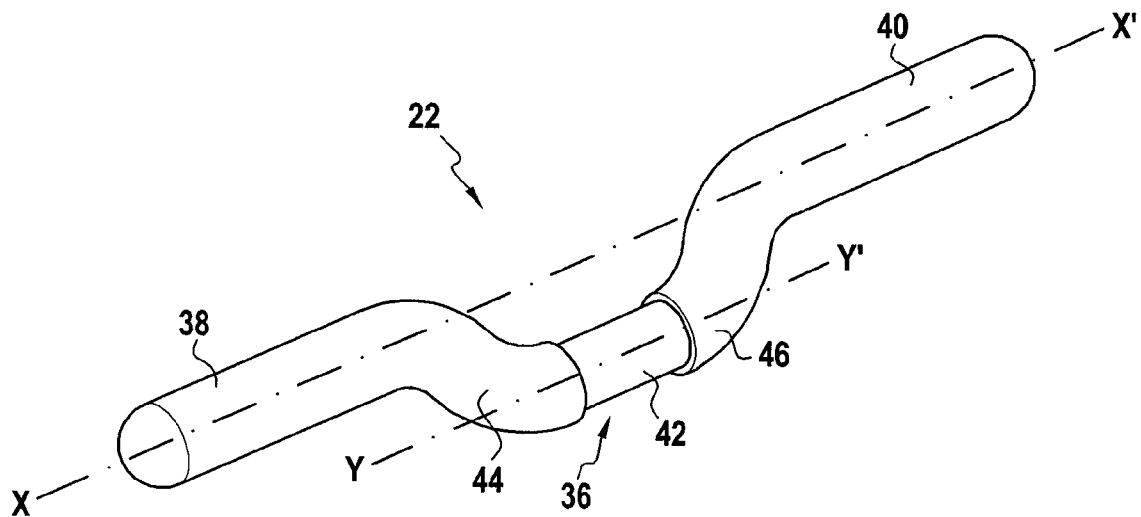
FIG. 5 is a perspective view of the connection bar.

With reference now to FIG. 5, there follows a more detailed description of a preferred embodiment of the connection bar 22 which constitutes an essential element of the invention. The fastener ends 38 and 40 of the bar are of circular right section, and these ends are in alignment on a common geometrical axis X,X'. In contrast, the middle portion 36 of the bar that co-operates with the bottom end of the spacer 20 presents an axis Y,Y' that is parallel to the axis X,X' but that is offset relative thereto. More precisely, the middle portion 36 comprises a cylindrical portion of smaller diameter 42 and two S-bend portions 44 and 46 connecting it to the two fastener ends 38 and 40.

With reference now to FIGS. 2A, 2B, 2C, and 3, there follows a description of a preferred embodiment of the fastener devices 24 and 26 for fastening the connection bar 22 to the sacrum. Since the two fastener devices are identical, only the device 24 is described.

In the embodiment shown in the figures, it is constituted essentially by a bottom bone screw 50 and a top screw 52. The bottom bone screw 50 is fitted with a shoe 54 that comprises a head 56 and a connection rod portion 58. The head 56 of the shoe 54 has a semicylindrical recess suitable for receiving the fastener end 40 of the connection bar 22. A locking member 60 that locks when tightened serves to hold the end of the connection bar 22 and prevent it from turning relative to the screw 50. The head 62 of the top screw 52 is also provided with a semicylindrical recess 64 that is suitable for receiving the end of the connection rod 58 of the shoe 54. A second locking member 66 serves to prevent the connection rod 58 from turning relative to the head of the screw 52. The fastener assemblies 24 and 26 constitute elements for anchoring in the sacrum each constituted essentially by the screws 50 and 52 and by the shoe 54. This provides very effective anchoring of the ends of the connection bar 22 in the sacrum. Nevertheless, the fastener device 24 and 26 could naturally be simplified without going beyond the invention. They could have no more than one bone screw 52 in each fastener device replacing the bone screw 50. The fastener ends 38 and 40 of the connection bar 22 would then be engaged directly in the heads of the bone screw 52.

Figure 4A:
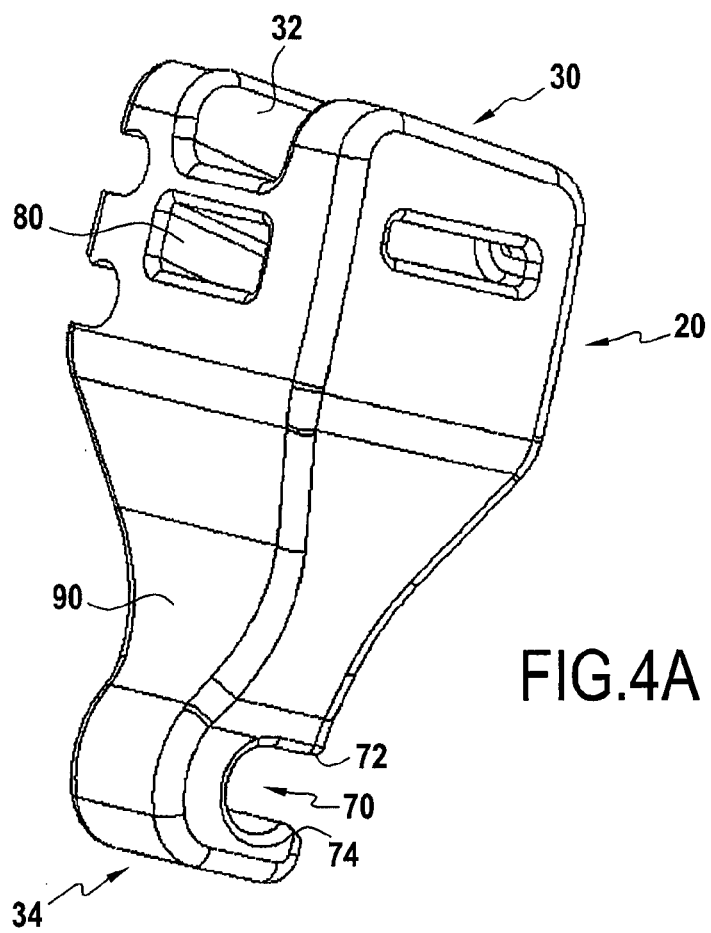
FIGS. 4A and 4B are perspective views of the spacer from two different angles.
Figure 4B:
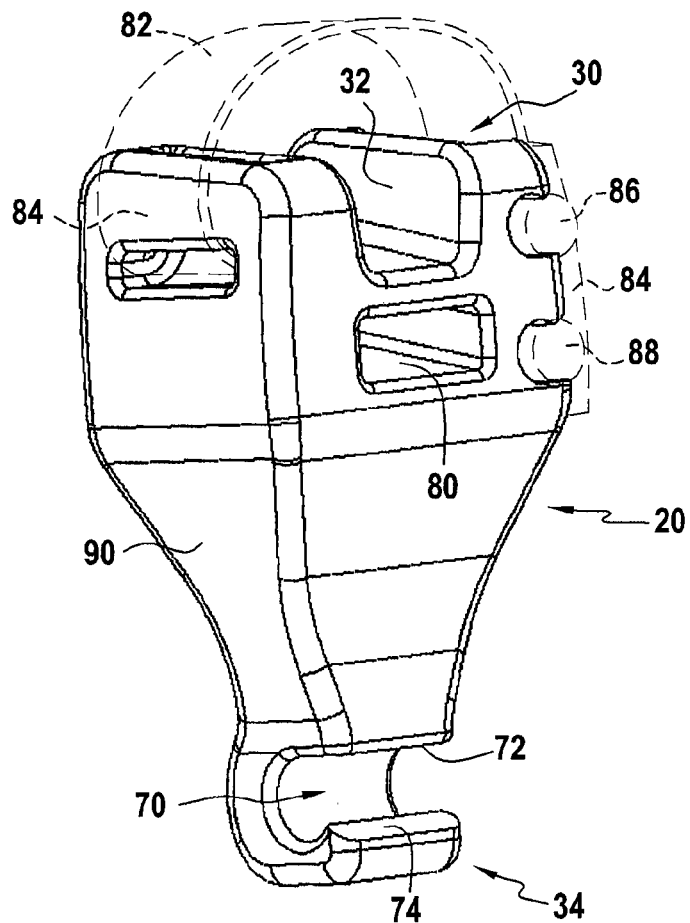

With reference now more particularly to FIGS. 4A and 4B, there follows a description of the bottom end 34 of the intervertebral spacer 20.

As mentioned above, the bottom end 34 of the spacer co-operates with the middle portion 36 of the connection bar 22. Preferably, the bottom end 34 of the spacer includes a housing 70 of substantially circular right section provided with a lateral slot 72 to enable the middle portion 36 of the connection bar to be inserted, and more precisely to enable its smaller-diameter portion 42 to be inserted. One of the edges of the insertion slot 72 constitutes a snap-fastener 74 in such a manner that the smaller-diameter portion 42 can be engaged in the housing 70 by elastically deforming the snap-fastener 74. In addition, the diameter of the right section of the housing 70 is very slightly greater than the diameter of the smaller-diameter portion 42 of the connection bar. Thus, after the smaller-diameter portion 42 of the connection bar has been engaged in the housing 70, the spacer 20 can pivot freely about the second axis Y,Y' of the bar. Nevertheless, because of the presence of the snap-fastener 74, the spacer remains fastened at its bottom end to the bar.

The top end 30 of the spacer 20 essentially comprises a recess 32 as mentioned above for receiving the spinous process 10 of lumbar vertebra L5. As shown in FIGS. 4A and 4B, the body of the spacer preferably includes a recess passing right through it and referenced 80, serving to confer a certain amount of resilience to the body of the intervertebral spacer. As is well known, it is necessary to secure the top end 30 of the spacer to the spinous process 10. This is preferably done by providing a flexible tie 82 having a first end 84 secured to one of the edges of the recess 32. On the opposite face of the spacer body there is provided a self-locking device 84 that is fastened to the spacer, preferably by a snap-fastener system 86, 88. The free end of the tie 82 is engaged in the self-locking device 84, and by pulling on said free end, the surgeon secures the spinous process in the top housing 32.

The steps performed by the surgeon for putting the implant into place are described below.

Initially, the surgeon screws the bottom bone screw 50 and the top bone screw 52 into the sacrum and mounts the shoes 54 on the heads of the bottom screws 50. The locking members 66 are tightened so that the screws 50 and 52 are effectively united via the shoes 54. In the following step, the fastener ends 38 and 40 of the connection bar 22 are engaged in the semicylindrical recesses of the shoes 54. Since the ends 38 and 40 of the bar are of circular right section, the middle portion 36 of the bar can pivot freely about the axis X,X' of said bar relative to the fastener devices 24 and 26. By means of this freedom to pivot, the middle portion 36 of the bar can be moved away from the sacrum to make it easier to engage the smaller-diameter portion 42 of the bar in the snap-fastening recess 70. After the bottom end of the spacer has been engaged on the bar by snap-fastening, it is possible to cause the middle portion of the bar to pivot in such a manner that the anterior face 90 of the spacer body bears effectively against the sacrum. As shown in FIGS. 4A and 4B, the anterior face 90 of the spacer body is not plane. It is shaped to fit as well as possible to the shape of the sacrum.

In addition, since the spacer 20 can pivot freely about the axis Y,Y' of the middle portion of the bar 22, it becomes much easier to engage the spinous process of the fifth lumbar vertebra in the top housing 32 of the spacer. This ability of the spacer to pivot relative to the bar and of the bar to pivot relative to the fastener devices 24 and 26 in the sacrum enables the spacer 20 to be properly positioned. In particular, the bottom end of the spacer can be "wedged" between the middle portion 36 of the bar engaged in the housing 70 and the posterior face of the sacrum. When the suitable position is obtained for the spacer 20 and consequently the suitable position is also obtained for the connection bar 22, then the locking members 60 of the shoes 54 are tightened so that the bar 22 is prevented from moving relative to the fastener device 24 and 26, and thus relative to the sacrum.

It then remains for the surgeon to put the tie 82 into place over the spinous process and exert traction on the free end of the tie so as to tighten the tie around the process and thus secure the top end of the spacer 20 to the process.

What is claimed is:

1. An implant for placing between the sacrum of a patient and the fifth lumbar vertebra, the implant comprising:
   a connection bar having two ends and a middle portion connected to said two ends;
   means for fastening each end of the connection bar to the sacrum; and
   a spacer having a recess disposed in a first end for receiving the spinous process of the fifth lumbar vertebra, and a second end co-operating with said middle portion;
   the two ends of said connection bar lying on a common first geometrical axis, said middle portion lying on a second geometrical axis parallel to the first geometrical axis but offset relative therefrom;
   wherein said second end of the spacer includes a recess for receiving the middle portion of the connection bar, said recess allowing said spacer to pivot freely about the second geometrical axis of the middle portion of the connection bar;
   wherein said second end of the spacer includes snap-fastener means for fastening the spacer on the middle portion of the connection bar.

2. An implant according to claim 1, wherein the ends of said connection bar are of circular cross-section and each fastener means for fastening the connection bar to the sacrum includes a head suitable for pivotally receiving one of the ends of said bar and a locking member suitable, in its active position, for preventing said end of the bar from pivoting.

3. An implant according to claim 2, wherein each fastener means further comprises a threaded portion for screwing into the sacrum, and said head includes an open semicylindrical recess for receiving a cylindrical end of said bar.

4. An implant according to claim 1, wherein said spacer has a first face facing towards the vertebral column and a second face opposite from the first face, said first face being non-planar so as to match the shape of the sacrum against which the spacer bears.

5. An implant according to claim 1, wherein the two ends of the connection bar comprise a first end portion and a second end portion, each of the first and second end portions extending along the common first geometrical axis.

6. An implant according to claim 5, wherein the first and second end portions are cylindrical, each of the first and second end portions having a central axis extending therethrough that is coaxial with the common first geometrical axis.

7. An implant according to claim 1, wherein the middle portion is cylindrical, the middle portion having a central axis extending therethrough that is coaxial with the second geometrical axis.

8. An implant for placing between the sacrum of a patient and the fifth lumbar vertebra, the implant comprising:
   a connection bar having two ends and a middle portion connected to said two ends;
   means for fastening each end of the connection bar to the sacrum; and
   a spacer having a recess disposed in a first end for receiving the spinous process of the fifth lumbar vertebra, and a second end co-operating with said middle portion;
   the two ends of said connection bar lying on a common first geometrical axis, said middle portion lying on a second geometrical axis parallel to the first geometrical axis but offset relative therefrom;
   wherein said second end of the spacer includes a recess for receiving the middle portion of the connection bar, said recess allowing said spacer to pivot freely about the second geometrical axis of the middle portion of the connection bar;
   wherein the recess provided at the second end of said spacer is of a size and cross-section that is sufficient to receive the middle portion of the connection bar to pivot freely, and the spacer further includes a slot for inserting the connection bar into the recess, the slot being of a size relative to a cross-sectional size of the middle portion of the connection bar that is such as to produce a snap-fastening effect.

* * * * *